United States Patent
Tanaka et al.

(12) 
(10) Patent No.: US 6,555,633 B1
(45) Date of Patent: Apr. 29, 2003

(54) CATALYSTS FOR α-OLEFIN PRODUCTION AND PROCESSES FOR PRODUCING α-OLEFIN

(75) Inventors: Shinji Tanaka, Yamaguchi (JP); Yasushi Shiraki, Yamaguchi (JP); Takao Tamura, Yamaguchi (JP); Masahiko Kuramoto, Ichihara (JP); Haruhito Sato, Ichihara (JP); Masami Watanabe, Ichihara (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 0 days.

(21) Appl. No.: 09/623,974

(22) PCT Filed: Jan. 7, 2000

(86) PCT No.: PCT/JP00/00042

§ 371 (c)(1), (2), (4) Date: Sep. 11, 2000

(87) PCT Pub. No.: WO00/43123

PCT Pub. Date: Jul. 27, 2000

(30) Foreign Application Priority Data

Jan. 21, 1999 (JP) .............................. 11-013186
Feb. 19, 1999 (JP) .............................. 11-041334

(51) Int. Cl.[7] .................................. C08F 4/42
(52) U.S. Cl. .................. 526/160; 526/126; 526/362; 526/943; 526/158; 502/152; 502/80
(58) Field of Search .................... 526/160, 943, 526/352, 126, 158; 502/152, 80

(56) References Cited

U.S. PATENT DOCUMENTS

| | | | |
|---|---|---|---|
| 4,172,053 A | * 10/1979 | Vogt et al. | .................. 502/175 |
| 4,579,832 A | * 4/1986 | Shabtai et al. | ................. 502/84 |
| 4,722,918 A | * 2/1988 | Schneider et al. | ............ 502/81 |
| 5,360,775 A | * 11/1994 | Suda et al. | .................... 502/84 |
| 5,461,127 A | 10/1995 | Naganuma et al. | |
| 5,629,398 A | 5/1997 | Okamoto et al. | |
| 5,648,443 A | 7/1997 | Okamoto et al. | |
| 5,693,728 A | 12/1997 | Okamoto et al. | |
| 5,854,165 A | 12/1998 | Yabunouchi et al. | |
| 6,171,994 B1 | 1/2001 | Yabunouchi et al. | |
| 6,339,135 B1 | 1/2002 | Kashiwamura et al. | |

FOREIGN PATENT DOCUMENTS

| | | | |
|---|---|---|---|
| EP | 0 511 665 A2 | * | 11/1992 |
| EP | 0 511 665 | * | 11/1992 |
| EP | 511 665 | | 11/1992 |
| EP | 524 733 | | 1/1993 |
| EP | 0 524 733 A1 | * | 1/1993 |
| JP | 10-80639 | | 3/1998 |
| JP | 11-1508 | * | 1/1999 |
| JP | 11-1508 | | 6/1999 |
| WO | WO 94/28034 | * | 12/1994 |
| WO | WO 96/23010 | | 8/1996 |

* cited by examiner

*Primary Examiner*—David W. Wu
*Assistant Examiner*—Ling-Siu Choi
(74) *Attorney, Agent, or Firm*—Oblon, Spivak, McClelland, Maier & Neustadt, P.C.

(57) ABSTRACT

A catalyst which is able to express a high oligomerizing activity of ethylene and a method for the production of α-olefin where ethylene is oligomerized using said catalyst are provided. The present invention relates to a catalyst for the production of α-olefin obtained by contacting (a) clay, clay mineral or ion-exchange layer compound with (b-1) a transition metal complex of Groups 4 to 6 of the Periodic Table and also relates to a method for the production of α-olefin by oligomerization of ethylene using said catalyst. The present invention further relates to a catalyst for the production of α-olefin obtained by contacting (a) clay, clay mineral or ion-exchange layer compound with (b-2) a transition metal complex of Groups 8 to 10 of the Periodic Table and also relates to a method of the production of α-olefin by oligomerization of ethylene using said catalyst.

15 Claims, No Drawings

CATALYSTS FOR α-OLEFIN PRODUCTION AND PROCESSES FOR PRODUCING α-OLEFIN

BACKGROUND OF THE INVENTION

1. Field of the Invention

The present invention relates to a catalyst for the production of α-olefin and also to a method for the production of α-olefin. More particularly, it relates to a catalyst by which α-olefin can be efficiently produced and also to a method for the production of α-olefin by means of oligomerization of ethylene using the said catalyst.

2. Description of the Related Art

In the production of α-olefin by oligomerization of ethylene, a method in which a transition metal complex is used as a main catalytic component while an oxygen-containing organoaluminum compound such as alumoxane or a boron compound such as perfluorotetraphenyl borate is used as a co-catalyst has been known already. However, the necessary amount of such a co-catalyst to the main catalyst is usually several hundred times moles whereby the activity per catalyst is low and the productivity is bad. In addition, the yield of $C_6$, $C_8$ and $C_{10}$ components which are highly demanded is insufficient.

The present invention has been achieved in view of the above and an object of the present invention is to provide a catalyst which is able to express a high oligomerizing activity to ethylene and also to provide a method for the production of α-olefin by oligomerization of ethylene using the catalyst.

In the present invention, α-olefin (oligomer) stands for a polymer having a molecular weight of 10,000 or less and is different from common high molecular substances having higher molecular weight and expressing the characteristics inherent to the high molecular substances. Accordingly, the property demanded for the catalyst used for the production of α-olefin (oligomer) is different from the property demanded for the catalyst for the production of high molecular substances. Consequently, it is not true that a catalyst for the production of high molecular substances (polyolefins) can always be used for the production of α-olefin as it is.

SUMMARY OF THE INVENTION

The present inventors have found that the above-mentioned object can be effectively achieved by the use of a transition metal complex of Groups 4 to 6 of the Periodic Table or a transition metal complex of Groups 8 to 10 of the Periodic Table as a main catalyst and also by the use of clay, claymineral or ion-exchange layer compound as a co-catalyst whereby the present inventors have accomplished the present invention.

The present invention may be divided into the first feature using a transition metal complex of Groups 4 to 6 of the Periodic Table as a main catalyst and the second feature using a transition metal complex of Groups 8 to 10 of the Periodic Table as a main catalyst. As a result of adoption of the first feature, the above-mentioned object can be achieved and high yield of $C_6$, $C_8$ and $C_{10}$ components can be achieved as well. As a result of adoption of the second feature, the above-mentioned object can be achieved and production of by-products such as heavy-weight components and wax component can be held to a low level.

Thus, the gist of the present invention is as follows.

The first feature of the present invention relates to:

(1) a catalyst for the production of α-olefin obtained by contacting (a) clay, clay mineral or ion-exchange layer compound with (b-1) a transition metal complex of Groups 4 to 6 of the Periodic Table;

(2) the catalyst for the production of α-olefin according to the above (1), wherein ligand of the transition metal complex which is the component (b-1) has a conjugated five-membered ring;

(3) the catalyst for the production of α-olefin according to the above (1) or (2), wherein the transition metal in the component (b-1) is zirconium;

(4) the catalyst for the production of α-olefin according to any of the above (1) to (3), wherein the clay, the clay mineral or the ion-exchange layer compound which is the component (a) contains an inorganic substance containing phyllosilicate;

(5) the catalyst for the production of α-olefin according to any of the above (1) to (4), wherein the clay, the clay mineral or the ion-exchange layer compound which is the component (a) is montmorillonite;

(6) the catalyst for the production of α-olefin according to any of the above (1) to (5), wherein the clay, the clay mineral or the ion-exchange layer compound which is the component (a) is that which is treated with an organosilane compound; and (7) a method for the production of α-olefin, characterized in that, ethylene is oligomerized using the catalyst for the production of α-olefin which is mentioned in any of the above (1)–(6).

The second feature of the present invention relates to:

(8) a catalyst for the production of α-olefin obtained by contacting (a) clay, clay mineral or ion-exchange layer compound with (b-2) a transition metal complex of Groups 8 to 10 of the Periodic Table;

(9) the catalyst for the production of α-olefin according to the above (8), wherein ligand of the transition metal complex which is the component (b-2) has a carbon-nitrogen unsaturated bond;

(10) the catalyst for the production of α-olefin according to the above (8) or (9), wherein the clay, the clay mineral or the ion-exchange layer compound which is the component (a) contains an inorganic substance containing phyllosilicate;

(11) the catalyst for the production of α-olefin according to any of the above (8) to (10), wherein the clay, the clay mineral or the ion-exchange layer compound which is the component (a) is montmorillonite; and

(12) a method for the production of α-olefin, characterized in that, ethylene is oligomerized using the catalyst for the production of α-olefin which is mentioned in any of the above (8)–(11).

DETAILED DESCRIPTION OF THE INVENTION

The present invention will be further illustrated hereunder.

The catalyst for the production of α-olefin in accordance with the present invention is obtained by contacting (a) clay, clay mineral or ion-exchange layer compound (which maybe referred to as "clay or the like" hereinafter) with (b-1) a transition metal complex of Groups 4 to 6 of the Periodic Table. The catalyst for the production of α-olefin in accordance with the present invention is also obtained by contacting the above-mentioned component (a) with (b-2) a transition metal complex of Groups 8 to 10 of the Periodic Table.

Those components (a), (b-1) and (b-2) will be illustrated in detail hereunder.

Component (a)

The component (a) is clay, clay mineral or ion-exchange layer compound. As one of the component (a), clay or clay mineral is used. Clay is an aggregate of fine aqueous silicate mineral and has such a property that, when it is kneaded after addition of an appropriate amount of water, it results in a plasticity and, when dried, it shows a rigidity while, when burned at high temperature, it is sintered. Clay mineral is an aqueous silicate which is a main component of clay. In the preparation of the catalyst for the production of $\alpha$-olefin according to the present invention, any of clay and claymineral may be used and that may be either a natural one or synthetic one.

It is also possible to use an ion-exchange layer compound as the component (a). The ion-exchange layer compound is a compound having such a crystalline structure that the planes constituted by ionic bond or the like are layered each other in parallel by a weak bonding force and that the ion contained therein is exchangeable. Some clay minerals are ion-exchange layer compounds.

As specific examples of the component (a), mentioned are, for example, phyllosilicic acid compounds belong to clay minerals. Phyllosilicic acid compounds include phyllosilicic acid and phyllosilicates. As natural phyllosilicates, known are montmorillonite, saponite and hectorite of the smectite family; illite and sericite of the mica family; and mixed layer minerals of smectites and micas, or those of micas and vermiculites.

As synthetic products, known are fluoro-tetrasilicon mica (TSM), laponite, smectone, etc.

Also mentioned are ion-exchanging compounds having a layered crystal structure, such as $\alpha$-Zr(HPO$_4$)$_2$, $\gamma$-Zr(HPO$_4$)$_2$, $\alpha$-Ti(HPO$_4$)$_2$ and $\gamma$-Ti(HPO$_4$)$_2$, etc. These are not clay minerals.

Examples of clay and clay minerals which do not belong to ion-exchanging layered compounds include clay having a low montmorillonite content and referred to as bentonite; kibushi clay comprising montmorillonite and many other components; gairome clay; sepiolite and palygorskite having a fibrous morphology; and amorphous or low-crystalline allophane, and imogolite.

Before contacting the component (a) with the component (b-1) or (b-2), it is preferred for the component (a) to subject to a chemical treatment for removing the impurities in clay, clay mineral and ion-exchange layer compound and for making into a more favorable form as a catalyst component by modifying its structure and function.

In the chemical treatment, there are a surface treatment whereby impurities attached on the surface of clay or the like is removed and a treatment whereby the crystal structure of the clay or the like is affected. Specific examples are a treatment with acid, a treatment with alkali, a treatment with salt, a treatment with organic substance, etc.

As a result of the treatment with acid, impurities on the surface are removed and, at the same time, cations such as aluminum, iron and magnesium in the crystal structure of the clay or the like are eluted whereby the surface area can be increased. It is also possible that, by the treatment with alkali, the crystal structure of the clay or the like can be modified into a favorable form. In the treatment with salt or with organic substance, it is further possible that ionic complex, molecular complex, organic complex, etc. are produced on the clay or the like whereby its surface area, interlayer distance, etc. are modified to a favorable form. To be more specific, it is possible to produce an intercalation compound where the distance between layers is expanded by substituting of the exchangeable ion between the layers with other bulky ion utilizing the ion-exchanging property of the clay or the like for example.

It is preferred that the chemically treated clay or the like as above is further treated with an organosilane compound for further enhancement of the catalytic activity. An example of the organosilane compound is a compound which is represented by the following formula.

$$R_nSiX_{4-n}$$

[In the formula, R is a substituent where an atom at the site directly bonding with a silicon atom is a carbon atom, a silicon atom or a hydrogen atom; X is a substituent where an atom at the site directly bonding to a silicon atom is a halogen atom, an oxygen atom or a nitrogen atom; R or X may be the same or different in the case there are two or more R or X; and n is an integer of 1–3.]

The said organosilane compound may be in a form of a bis-silyl substance represented by the following formula $$X_{4-n}Si\,(CH_2)_m SiX_{4-n}$$

[In the formula, m is 1–10 and n is 1–3] or may be in a form of a polynuclear polysiloxane, polysilazane, etc.

The silane compounds represented by the above-mentioned formula include, for example, trialkylsilyl chlorides such as trimethylsilyl chloride, triethylsilyl chloride, triisopropylsilyl chloride, tert-butyldimethylsilyl chloride, tert-butyldiphenylsilyl chloride, phenethyldimethylsilyl chloride, etc.; dialkylsilyl dichlorides such as dimethylsilyl dichloride, diethylsilyl dichloride, diisopropylsilyl dichloride, di-n-hexylsilyl dichloride, dicyclohexylsilyl dichloride, docosylmethylsilyl dichloride, bis(phenethyl) silyl dichloride, methylphenethylsilyl dichloride, diphenylsilyl dichloride, dimethylsilyl dichloride, ditolylsilyl dichloride, etc.; diarylsilyl dichlorides; alkylarylsilyl dichlorides.

Other examples are silyl halides where the chloride moiety in the above-mentioned compounds is substituted with other halogen atom; disilazanes such as bis(trimethylsilyl) amide, bis(triethylsilyl)amide, bis(triisopropylsilyl)amide, bis(dimethylethylsilyl)amide, bis(diethylmethylsilyl)amide, bis(dimethylphenylsilyl)amide, bis(dimethyltrisilyl)amide and bis(dimethylmesitylsilyl)amide; trialkylsilyl hydroxides such as trimethylsilyl hydroxide, triethylsilyl hydroxide, triisopropylsilyl hydroxide, tert-butyldimethylsilyl hydroxide and phenyldimethylsilyl hydroxide; polysilanols known by a common name of peralkyl polysiloxypolyols; bis-silyls such as bis(methyldichlorosilyl)methane, 1,2-bis (methyldichlorosilyl)ethane, bis(methyldichlorosilyl)octane and bis(triethoxysilyl)ethane; and silanes having hydride such as dimethylchlorosilane, (N,N-dimethylamino) dimethylsilane and diisobutylchlorosilane. Each of those organosilane compounds may be used either solely or jointly by combining two or more thereof.

Among those organosilane compounds, those having at least one alkyl group which is directly bonded to a silicon atom are preferred and alkylsilyl halides or, particularly, dialkylsilyl dihalides are favorably used.

Treatment with such an organosilane compound is effective when carried out in the presence of water. In that case, it is presumed that water has an action that it destroys the crystal structure (particularly, the layered structure) of the clay or the like and enhances the contacting efficiency between the organosilane compound and the clay or the like, that is, water enlarges the interlayers of the crystals of the clay or the like and accelerates diffusion of the organosilane compound into the crystals in the layers is promoted.

With regard to the component (a), the preferred one is that where the pore volume having a radius of 20 Å or more as measured by mercury porosimetry is not less than 0.1 ml/g or, particularly, 0.2–5.5 ml/g.

The component (a) may be used as it is or may be used after water is freshly added thereto and adsorbed therewith or after being heated and dehydrated.

The component (a) may be used either solely or jointly by combining two or more.

Among the component (a), clay or clay mineral is preferred and, to be more specific, phyllosilicate is preferred, smectites are particularly preferred and montmorillonite is far more preferred.

Component (b-1)

The component (b-1) which is a transition metal complex of Groups 4 to 6 of the Periodic Table is not limited to metallocene which is a group of organometallic complex compounds but may be selected from organometallic complexes of a broad range although metallocene is suitable. Among the transition metals of Groups 4 to 6 of the Periodic Table, those of Group 4 of the Periodic Table is preferred and zirconium is particularly preferred.

As the component (b-1), preferred are those of the following general formulae (1) to (3). However, the component (b-1) is not limited to the formulae.

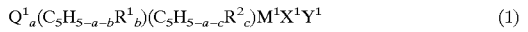

$$Q^1{}_a(C_5H_{5-a-b}R^1{}_b)(C_5H_{5-a-c}R^2{}_c)M^1X^1Y^1 \quad (1)$$

$$Q^2{}_a(C_5H_{5-a-d}R^3{}_d)Z^1M^1X^1Y^1 \quad (2)$$

$$(C_5H_{5-e}R^4{}_e)M^1X^1Y^1W^1 \quad (3)$$

where $Q^1$ represents a bonding group that crosslinks the two conjugated five-membered cyclic ligands $(C_5H_{5-a-b}R^1{}_b)$ and $(C_5H_{5-a-c}R^2{}_c)$;

$Q^2$ represents a bonding group that crosslinks the conjugated five-membered cyclic ligand $(C_5H_{5-a-d}R^3{}_d)$ and the group $Z^1$;

$(CH_{5-e}R^4{}_e)$ represents a conjugated five-membered cyclic ligand;

$R^1$, $R^2$, $R^3$ and $R^4$ each represent a hydrocarbon group, a halogen atom, an alkoxy group, a silicon-containing hydrocarbon group, a phosphorus-containing hydrocarbon group, a nitrogen-containing hydrocarbon group, or a boron-containing hydrocarbon group;

a represents 0, 1 or 2;

b, c and d each represent an integer of from 0 to 5 when a=0, or an integer of from 0 to 4 when a=1, or an integer of from 0 to 3 when a=2;

e represents an integer of from 0 to 5;

$M^1$ represents a transition metal of Groups 4 to 6 of the Periodic Table;

$X^1$, $Y^1$, $Z^1$, and $W^1$ each represent a covalent-bonding ligand; and $X^1$, $Y^1$, and $W^1$ may be bonded to each other to form a cyclic structure.

Specific examples of $Q^1$ and $Q^2$ include an alkylene group having from 1 to 4 carbon atoms, or a cycloalkylene group, or the group substituted by a lower alkyl or phenyl group at its side chain, such as a methylene group, an ethylene group, an isopropylene group, a methylphenylmethylene group, a diphenylmethylene group, a cyclohexylene group, etc.; a silylene group, or an oligosilylene group, or the group substituted by a lower alkyl or phenyl group at its side chain, such as a silylene group, a dimethylsilylene group, a methylphenylsilylene group, a diphenylsilylene group, a disilylene group, a tetramethyldisilylene group, etc.; and a hydrocarbon group (e.g., a lower alkyl group, a phenyl group, a hydrocarbyloxy group (preferably, a lower alkoxy group), etc.) containing germanium, phosphorus, nitrogen, boron or aluminium, such as a $(CH_3)_2Ge$ group, a $(C_6H_5)_2Ge$ group, a $(CH_3)_2P$ group, a $(C_6H_5)_2P$ group, a $(C_4H_9)N$ group, a $(C_6H_5)N$ group, a $(CH_3)B$ group, a $(C_4H_9)B$ group, a $(C_6H_5)B$ group, a $(C_6H_5)Al$ group, a $(CH_3O)Al$ group, etc. Of those, preferred are alkylene groups and silylene groups from an aspect of activity.

$(C_5H_{5-a-b}R^1{}_b)$, $(C_5H_{5-a-c}R^2{}_c)$, $(C_5H_{5-a-d}R^3{}_d)$, and $(C_5H_{5-e}R^4{}_e)$ are conjugated, 5-membered cyclic ligands, in which $R^1$, $R^2$, $R^3$, and $R^4$ each represent a hydrocarbon group, a halogen atom, an alkoxy group, a silicon-containing hydrocarbon group, a phosphorus-containing hydrocarbon group, a nitrogen-containing hydrocarbon group, or a boron-containing hydrocarbon group; a represents 0, 1 or 2; b, c and d each represent an integer of from 0 to 5 when a=0, or an integer of from 0 to 4 when a=1, or an integer of from 0 to 3 when a=2; and e represent an integer of from 0 to 5. The hydrocarbon group preferably has from 1 to 20 carbon atoms, more preferably from 1 to 12 carbon atoms. The hydrocarbon group may be a monovalent one that bonds to the cyclopentadienyl group of a conjugated, 5-membered cyclic group. Two of plural hydrocarbon groups, if any, maybe bonded to each other to form a cyclic structure along with a part of the cyclopentadienyl group. Specific examples of those conjugated, 5-membered cyclic ligands are substituted or unsubstituted cyclopentadienyl groups, indenyl groups and fluorenyl groups. The halogen atom includes chlorine, bromine, iodine and fluorine atoms. The alkoxy group preferably has from 1 to 12 carbon atoms. The silicon-containing hydrocarbon group includes, for example, groups of $—Si(R^5)(R^6)(R^7)$, in which $R^5$, $R^6$ and $R^7$ each represent a hydrocarbon group having from 1 to 24 carbon atoms. As the phosphorus-containing hydrocarbon group, the nitrogen-containing hydrocarbon group and the boron-containing hydrocarbon group, for example, mentioned are groups of $—P(R^8)(R^9)$, $—N(R^8)(R^9)$, and $—B(R^8)(R^9)$, respectively, in which $R^8$ and $R^9$ each represent a hydrocarbon group having from 1 to 18 carbon atoms. Plural $R^1$'s, $R^2$'s, $R^3$'s and $R^4$'s, if any, may be the same or different ones, respectively. In formula (1), the conjugated, 5-membered cyclic ligands $(C_5H_{5-a-b}R^1{}_b)$ and $(C_5H_{5-a-c}R^2{}_c)$ may be the same or different ones.

$M^1$ represents a transition metal element of Groups 4 to 6 of the Periodic Table, including, for example, titanium, zirconium, hafnium, niobium, molybdenum, tungsten, etc. Of those, preferred are titanium, zirconium and hafnium.

$Z^1$ represents a covalent-bonding ligand, including, for example, an oxygen atom (—O—), a sulfur atom (—S—), an alkoxy group having from 1 to 20, preferably from 1 to 12 carbon atoms, a thioalkoxy group having from 1 to 20, preferably from 1 to 12 carbon atoms, a nitrogen-containing hydrocarbon group having from 1 to 40, preferably from 1 to 18 carbon atoms, and a phosphorus-containing hydrocarbon group having from 1 to 40, preferably from 1 to 18 carbon atoms.

$X^1$ and $Y^1$ each represent a covalent-bonding ligand, including, for example, a hydrogen atom, a halogen atom, a hydrocarbon group having from 1 to 20, preferably from 1 to 10 carbon atoms, an alkoxy group having from 1 to 20, preferably from 1 to 10 carbon atoms, an amino group, a phosphorus-containing hydrocarbon group having from 1 to 20, preferably from 1 to 12 carbon atoms (e.g., a diphenylphosphine group, etc.), a silicon-containing hydrocarbon group having from 1 to 20, preferably from 1 to 12 carbon atoms (e.g., a trimethylsilyl group, etc.), a hydrocarbon group having from 1 to 20, preferably from 1 to 12 carbon atoms, and a boron compound residue (e.g., $B(C_6H_5)_4$, $BF_4$). Of those, preferred are halogen atoms and hydrocarbon groups having from 1 to 20 carbon atoms. $X^1$, $Y^1$ and $Z^1$ may be the same or different ones.

As preferred specific examples of the transition metal compounds of formulae (1) and (2), mentioned are the following compounds, which have a conjugated five-membered cyclic ligand.

(i) Transition metal compounds not having a crosslinkable bonding group but having two conjugated, 5-membered cyclic ligands, such as bis(cyclopentadienyl)zirconium dichloride, bis(methylcyclopentadienyl)zirconium dichloride, bis(dimethylcyclopentadienyl)zirconium dichloride, bis(trimethylcyclopentadienyl)zirconium dichloride, bis(tetramethylcyclopentadienyl)zirconium dichloride, bis(pentamethylcyclopentadienyl)zirconium dichloride, bis(n-butylcyclopentadienyl)zirconium dichloride, bis(indenyl)zirconium dichloride, bis(fluorenyl)zirconium dichloride, bis(cyclopentadienyl)zirconium chlorohydride, bis(cyclopentadienyl)methylzirconium chloride, bis(cyclopentadienyl)ethylzirconium chloride, bis(cyclopentadienyl)phenylzirconium chloride, bis(cyclopentadienyl)dimethylzirconium, bis(cyclopentadienyl)diphenylzirconium, bis(cyclopentadienyl)dineopentylzirconium, bis(cyclopentadienyl)dihydrozirconium, (cyclopentadienyl)(indenyl)zirconium dichloride, (cyclopentadienyl)(fluorenyl)zirconium dichloride, etc.

(ii) Transition metal compounds having two conjugated, 5-membered cyclic ligands, in which the two ligands are crosslinked with an alkylene group, such as methylenebis(indenyl)zirconium dichloride, ethylenebis(indenyl)zirconium dichloride, methylenebis(indenyl)zirconium chlorohydride, ethylenebis(indenyl)methylzirconium chloride, ethylenebis(indenyl)methoxychlorozirconium, ethylenebis(indenyl)zirconium diethoxide, ethylenebis(indenyl)dimethylzirconium, ethylenebis(4,5,6,7-tetrahydroindenyl)zirconium dichloride, ethylenebis(2-methylindenyl)zirconium dichloride, ethylenebis(2,4-dimethylindenyl)zirconium dichloride, ethylenebis(2-methyl-4-trimethylsilylindenyl)zirconium dichloride, ethylenebis(2,4-dimethyl-5,6,7-trihydroindenyl)zirconium dichloride, ethylene(2,4-dimethylcyclopentadienyl)(3',5'-dimethylcyclopentadienyl)zirconium dichloride, ethylene(2-methyl-4-t-butylcyclopentadienyl)(3'-t-butyl-5'-methylcyclopentadienyl)zirconium dichloride, ethylene(2,3,5-trimethylcyclopentadienyl)(2',4',5'-trimethylcyclopentadienyl)zirconium dichloride, isopropylidenebis(2-methylindenyl)zirconium dichloride, isopropylidenebis(indenyl)zirconium dichloride, isopropylidenebis(2,4-dimethylindenyl)zirconium dichloride, isopropylidene(2,4-dimethylcyclopentadienyl)(3',5'-dimethylcyclopentadienyl)zirconium dichloride, isopropylidene(2-methyl-4-t-butylcyclopentadienyl)(3'-t-butyl-5'-methylcyclopentadienyl)zirconium dichloride, methylene(cyclopentadienyl)(3,4-dimethylcyclopentadienyl)zirconium dichloride, methylene(cyclopentadienyl)(3,4-dimethylcyclopentadienyl)zirconium chlorohydride, methylene(cyclopentadienyl)(3,4-dimethylcyclopentadienyl)dimethylzirconium, methylene(cyclopentadienyl)(3,4-dimethylcyclopentadienyl)diphenylzirconium, methylene(cyclopentadienyl)(trimethylcyclopentadienyl)-zirconium dichloride, methylene(cyclopentadienyl)(tetramethylcyclopentadienyl)-zirconium dichloride, isopropylidene(cyclopentadienyl)(3,4-dimethylcyclopentadienyl)zirconium dichloride, isopropylidene(cyclopentadienyl)(2,3,4,5-tetramethylcyclopentadienyl)zirconium dichloride, isopropylidene(cyclopentadienyl)(3-methylindenyl)zirconium dichloride, isopropylidene(cyclopentadienyl)(fluorenyl)zirconium dichloride, isopropylidene(2-methylcyclopentadienyl)(fluorenyl)zirconium dichloride, isopropylidene(2,5-dimethylcyclopentadienyl)(3,4-dimethylcyclopentadienyl)zirconium dichloride, isopropylidene(2,5-dimethylcyclopentadienyl)(fluorenyl)zirconium dichloride, ethylene(cyclopentadienyl)(3,5-dimethylcyclopentadienyl)zirconium dichloride, ethylene(cyclopentadienyl)(fluorenyl)zirconium dichloride, ethylene(2,5-dimethylcyclopentadienyl)(fluorenyl)zirconium dichloride, ethylene(2,5-diethylcyclopentadienyl)(fluorenyl)zirconium dichloride, diphenylmethylene(cyclopentadienyl)(3,4-diethylcyclopentadienyl)zirconium dichloride, diphenylmethylene(cyclopentadienyl)(3,4-diethylcyclopentadienyl)zirconium dichloride, cyclohexylidene(cyclopentadienyl)(fluorenyl)zirconium dichloride, cyclohexylidene(2,5-dimethylcyclopentadienyl)(3',4'-dimethylcyclopentadienyl)zirconium dichloride, etc.

(iii) Transition metal compounds having two silylene-crosslinked, conjugated, 5-membered cyclic ligands, such as dimethylsilylenebis(indenyl)zirconium dichloride, dimethylsilylenebis(4,5,6,7-tetrahydroindenyl)zirconium dichloride, dimethylsilylenebis(2-methylindenyl)zirconium dichloride, dimethylsilylenebis(2,4-dimethylindenyl)zirconium dichloride, dimethylsilylenebis(2,4-dimethylcyclopentadienyl)(3',5'-dimethylcyclopentadienyl)zirconium dichloride, dimethylsilylenebis(2-methyl-4,5-benzoindenyl)zirconium dichloride, dimethylsilylenebis(2-methyl-4-naphthylindenyl)zirconium dichloride, dimethylsilylenebis(2-methyl-4-phenylindenyl)zirconium dichloride, phenylmethylsilylenebis(indenyl)zirconium dichloride, phenylmethylsilylenebis(4,5,6,7-tetrahydroindenyl)zirconium dichloride, phenylmethylsilylenebis(2,4-dimethylindenyl)zirconium dichloride, phenylmethylsilylene(2,4-dimethylcyclopentadienyl)(3',5'-dimethylcyclopentadienyl)zirconium dichloride, phenylmethylsilylene(2,3,5-trimethylcyclopentadienyl)(2',4',5'-trimethylcyclopentadienyl)zirconium dichloride, phenylmethylsilylenebis(tetramethylcyclopentadienyl)-zirconium dichloride, diphenylsilylenebis(2,4-dimethylindenyl)zirconium dichloride, diphenylsilylenebis(indenyl)zirconium dichloride, diphenylsilylenebis(2-methylindenyl)zirconium dichloride, tetramethyldisilylenebis(indenyl)zirconium dichloride, tetramethyldisilylenebis(cyclopentadienyl)zirconium dichloride, tetramethyldisilylene(3-methylcyclopentadienyl)(indenyl)zirconium dichloride, dimethylsilylene(cyclopentadienyl)(3,4-dimethylcyclopentadienyl)zirconium dichloride, dimethylsilylene-(cyclopentadienyl)(trimethylcyclopentadienyl)zirconium dichloride, dimethylsilylene-(cyclopentadienyl)(tetramethylcyclopentadienyl)zirconium dichloride, dimethylsilylene(cyclopentadienyl)(3,4-diethylcyclopentadienyl)zirconium dichloride, dimethylsilylene-(cyclopentadienyl)

(triethylcyclopentadienyl)zirconium dichloride, dimethylsilylene-(cyclopentadienyl)(tetraethylcyclopentadienyl)zirconium dichloride, dimethylsilylene(cyclopentadienyl)(fluorenyl)zirconium dichloride, dimethylsilylene(cyclopentadienyl)(2,7-di-t-butylfluorenyl)zirconium dichloride, dimethylsilylene-(cyclopentadienyl)(octahydrofluorenyl)zirconium dichloride, dimethylsilylene(2-methylcyclopentadienyl)(fluorenyl)zirconium dichloride, dimethylsilylene(2,5-dimethylcyclopentadienyl)(fluorenyl)zirconium dichloride, dimethylsilylene(2-ethylcyclopentadienyl)(fluorenyl)zirconium dichloride, dimethylsilylene(2,5-diethylcyclopentadienyl)(fluorenyl)zirconium dichloride, diethylsilylene(2-methylcyclopentadienyl)(2',7'-di-t-butylfluorenyl)zirconium dichloride, dimethylsilylene(2,5-dimethylcyclopentadienyl)(2',7'-di-t-butylfluorenyl)zirconium dichloride, dimethylsilylene(2-ethylcyclopentadienyl)(2',7'-di-t-butylfluorenyl)zirconium dichloride, dimethylsilylene(diethylcyclopentadienyl)(2,7-di-t-butylfluorenyl)zirconium dichloride, dimethylsilylene-(methylcyclopentadienyl)(octahydrofluorenyl)zirconium dichloride, dimethylsilylene-(dimethylcyclopentadienyl)(octahydrofluorenyl)zirconium dichloride, dimethylsilylene-(ethylcyclopentadienyl)(octahydrofluorenyl)zirconium dichloride, dimethylsilylene-(diethylcyclopentadienyl)(octahydrofluorenyl)zirconium dichloride, etc.

(iv) Transition metal compounds having two conjugated, 5-membered cyclic ligands, in which the two ligands are crosslinked with a germanium-, aluminium-, boron-, phosphorus- or nitrogen-containing hydrocarbon group, such as dimethylgermylenebis(indenyl)zirconium dichloride, dimethylgermylene(cyclopentadienyl)(fluorenyl)zirconium dichloride, methylalumylenebis(indenyl)zirconium dichloride, phenylamylenebis(indenyl)zirconium dichloride, phenylphosphylenebis(indenyl)zirconium dichloride, ethylborylenebis(indenyl)zirconium dichloride, phenylamylenebis(indenyl)zirconium dichloride, phenylamylene(cyclopentadienyl)(fluorenyl)zirconium dichloride, etc.

(v) Transition metal compounds having one conjugated, 5-membered cyclic ligand, such as pentamethylcyclopentadienyl-bis(phenyl)aminozirconium dichloride, indenyl-bis(phenyl)aminozirconium dichloride, pentamethylcyclopentadienyl-bis(trimethylsilyl)aminozirconium dichloride, pentamethylcyclopentadienylphenoxyzirconium dichloride, dimethylsilylene(tetramethylcyclopentadienyl)tert-butylaminozirconium dichloride, dimethylsilylene(tetramethylcyclopentadienyl)-phenylaminozirconium dichloride, dimethylsilylene(tetrahydroindenyl)decylaminozirconium dichloride, dimethylsilylene(tetrahydroindenyl)-[bis(trimethylsilyl)amino]zirconium dichloride, dimethylgermylene-(tetramethylcyclopentadienyl)phenylaminozirconium dichloride, pentamethylcyclopentadienylzirconium trichloride, etc.

(vi) Transition metal compounds having two conjugated, 5-membered cyclic ligands in which the ligands are double-crosslinked, such as (1,1'-dimethylsilylene)(2,2'-isopropylidene)-bis(cyclopentadienyl)zirconium dichloride, (1,1'-dimethylsilylene)(2,2'-dimethylsilylene)-bis(cyclopentadienyl)zirconium dichloride, (1,1'-dimethylsilylene)(2,2'-isopropylidene)-bis(cyclopentadienyl)dimethylzirconium, (1,1'-dimethylsilylene)(2,2'-isopropylidene)-bis(cyclopentadienyl)dibenzylzirconium, (1,1'-dimethylsilylene)(2,2'-isopropylidene)-bis(cyclopentadienyl)bis(trimethylsilyl)zirconium, (1,1'-dimethylsilylene)(2,2'-isopropylidene)-bis(cyclopentadienyl)bis(trimethylsilylmethyl)zirconium, (1,2'-dimethylsilylene)(2,1'-ethylene)-bis(indenyl)zirconium dichloride, (1,1'-dimethylsilylene)(2,2'-ethylene)-bis(indenyl)zirconium dichloride, (1,1'-ethylene)(2,2'-dimethylsilylene)-bis(indenyl)zirconium dichloride, (1,1'-dimethylsilylene)(2,2'-cyclohexylidene)-bis(indenyl)zirconium dichloride, etc.

(vii) Derivatives from compounds of (i) to (vi) noted above, which are produced by substituting the chlorine atoms in those compounds of (i) to (vi) with any of bromine atoms, iodine atoms, hydrogen atoms, methyl groups, phenyl groups, benzyl groups, methoxy groups, dimethylamino groups and others, and/or by substituting the center metal, zirconium in those transition metal compounds with any of titanium, hafnium, niobium, molybdenum, tungsten and others.

Finally, the following compounds may be exemplified as the transition metal compound represented by the formula (3).

Thus, a transition metal compound having a conjugated five-membered cyclic ligand such as cyclopentadienylzirconium trichloride, methylcyclopentadienylzirconium trichloride, dimethylcyclopentadienylzirconium trichloride, trimethylcyclopentadienylzirconium trichloride, tetramethylcyclopentadienylzirconium trichloride, pentamethylcyclopentadienylzirconium trichloride, n-butylcyclopentadienylzirconium trichloride, indenylzirconium trichloride, fluorenylzirconium trichloride, tetrahydroindenylzirconium trichloride and octahydrofluorenylzirconium trichloride; a compound wherein the elemental atom in the above-mentioned compound is substituted with other halide, hydrogen, an alkyl group, an alkoxy group, etc.; and a compound wherein the zirconium which is a central metal is substituted with titanium or hafnium.

In addition, an example of a complex which is not able to be represented by the above formula is a chelate complex. Specific examples of the transition metal complex of Groups 4 to 6 of the Periodic Table are 2,2'-methylene-4,4',6,6'-tetra-tert-butyldiphenoxyzirconium dichloride, 2,2'-thio-4,4'-dimethyl-6,6'-di-tert-butyldiphenoxyzirconium dichloride and 2,2-isobutylidene-4,4',6,6'-tetramethyldiphenoxyzirconium dichloride. Further, the compounds where zirconium which is a central metal of such compounds is substituted with titanium or hafnium may be exemplified.

Among the above-mentioned compound groups, a group of the compounds listed under (i) is preferred and bis(cyclopentadienyl)zirconium chloride is particularly preferred.

The above (b-1) component may be used either solely or jointly by combining two or more.

Component (b-2)

The component (b-2) which is a transition metal complex of Groups 8 to 10 of the Periodic Table is not limited to metallocene which is a group of organometallic complex compounds but may be selected from organometallic complexes of a broad range.

As a preferred example of the transition metal complex of Groups 8 to 10 of the Periodic Table, that which is represented by the following formula (4) may be exemplified.

$$L^1L^2L^3M^2X^2{}_mY^2{}_n \qquad (4)$$

In the above formula, $M^2$ is a transition metal of Groups 8 to 10 of the Periodic Table and its specific examples are iron, cobalt, nickel, palladium and platinum while, among them, iron and cobalt are preferred. $L^1$ to $L^3$ each is a covalent complex having a carbon-nitrogen unsaturated bond and they may form a ring by bonding each other. $X^2$ and $Y^2$ each is a ligand of a covalent bond type or a ionic bond type and its specific examples are a hydrogen atom, a halogen atom, a hydrocarbon group having 1–20 (preferably, 1–10) carbon(s), an alkoxy group having 1–20 (preferably, 1–10) carbon(s), an amino group, a phosphorus-containing hydrocarbon group having 1–20 (preferably, 1–10) carbon (s) such as a diphenylphosphine group, and a boron compound containing a silicon-containing hydrocarbon group having 1–20 (preferably, 1–10) carbon(s) or halogen such as $BF_4$. Among them, a halogen atom and a hydrocarbon group having 1–20 carbon(s) are preferred. In the formula, $X^2$ and $Y^2$ may be the same or different and m and n each is an integer of 0–3.

Specific examples of the transition metal complex represented by the above formula (4) are iron or cobalt complex compounds in which a ligand is a 2,6-diacetylpyridine bisimine compound, a 2,6-diamidopyridine compound, a 2,6-diacetylaniline bisimine compound or the like. Among them, a complex with a 2,6-diacetylpyridine bisimine compound is preferred and its example is a complex compound represented by the following formula (5).

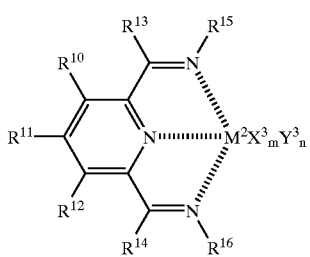

(5)

(In the formula, $R^{10}$ to $R^{14}$ each independently is a hydrogen atom or a hydrocarbon group having 1–20 carbon (s) and they may bond each other forming a ring; $R^{15}$ and $R^{16}$ each independently is an aliphatic hydrocarbon group having 1–20 carbon(s) or an aromatic group having a hydrocarbon group on the ring where the total carbon numbers are 7–20; $X^3$ and $Y^3$ each independently is a halogen atom or a hydrocarbon group having 1–20 carbon (s); and $M^2$ is a transition metal of Groups 8–10 of the Periodic Table.)

Examples of the hydrocarbon group having 1–20 carbon (s) for $R^{10}$–$R^{14}$ are a linear or branched alkyl group having 1–20 carbon(s), a cycloalkyl group having 3–20 carbons, an aryl group having 6–20 carbons and an aralkyl group having 7–20 carbons. Specific examples of the above linear or branched alkyl group having 1–20 carbon(s) are a methyl group, an ethyl group, an n-propyl group, an isopropyl group, an n-butyl group, an isobutyl group, a sec-butyl group, a tert-butyl group, various pentyl groups, various hexyl groups, various octyl groups, various decyl groups, various tetradecyl groups, various hexedecyl group and various octadecyl groups. Specific examples for the above cycloalkyl group having 3–20 carbons are a cyclopentyl group, a cyclohexyl group and a cyclooctyl group. Incidentally, an appropriate substituting group such as a lower alkyl group may be introduced into the ring of the cycloalkyl group. Specific examples of the aryl group having 6–20 carbons are a phenyl group, a tolyl group, a xylyl group, a naphthyl group and a methylnaphthyl group. Specific examples of the aralkyl group having 7–20 carbons are a benzyl group and a phenethyl group.

Examples of the aliphatic hydrocarbon group having 1–20 carbon(s) for $R^{15}$ and $R^{16}$ in the formula (5) are the same as those of the linear or branched alkyl group having 1–20 carbon(s) and the cycloalkyl group having 3–20 carbons for $R^{10}$ to $R^{14}$. Examples of the aromatic hydrocarbon group having a hydrocarbon group on the ring where the total carbons are 7–20 are the case where one or more linear, branched or cyclic alkyl group(s) having 1–10 carbon(s) is/are introduced into the aromatic ring such as a phenyl group or a naphthyl group. With regard to the said $R^{15}$ and $R^{16}$, an aromatic group having a hydrocarbon group on the ring is preferred and 2,4-dimethylphenyl group is particularly preferred.

Examples of the halogen atom for $X^3$ and $Y^3$ for the formula (5) are chlorine, bromine and iodine and, among them, chlorine is preferred. Examples of the hydrocarbon group having 1–20 carbon(s) for $X^3$ and $Y^3$ are as same as those for the above explanation in the case of $R^{10}$ to $R^{14}$.

The above-mentioned component (b-2) may be used solely or two or more may be used jointly.

Now, a method for the preparation of a catalyst for the production of α-olefin by contacting the component (a) with the component (b-1) mentioned above and also a method for the preparation of a catalyst for the production of α-olefin by contacting the component (a) with the component (b-2) mentioned above will be explained hereunder. A contacting treatment of those two components may be carried out in air although it is preferred to carry out in a stream of inert gas such as argon and nitrogen. It is also preferred to carry it out in a hydrocarbon such as pentane, hexane, heptane, toluene and xylene. It is further preferred to carry it out in a system where a compound having an active hydrogen such as a hydroxyl group and an amino group is not present. To this end, it is recommended that water and a compound having active hydrogen are previously removed from the system using an alkylating agent of a component (c) which will be mentioned later. Thus, it is recommended to use a product which is prepared by contacting (a), (b-1) and (c) or by contacting (a), (b-2) and (c) as a catalyst. Incidentally, it is not always necessary to use the component (c) at the stage of preparation of the catalyst but the component may be used in an oligomerization reaction system at the stage of production of α-olefin.

Although an organozinc zinc compound or an organomagnesium compound may be used as an alkylating agent for the above component (c), an organoaluminum compound which is available at a low cost is preferred. Its specific examples are trialkyl aluminum such as trimethyl aluminum, triethyl aluminum, tripropyl aluminum, triisobutyl aluminum and tri-tert-butyl aluminum; halogen- or alkoxy-containing alkyl aluminum such as dimethyl aluminum chloride, diethyl aluminum chloride, dimethyl aluminum methoxide and diethyl aluminum ethoxide; and alumoxane such as methyl alumoxane, ethyl alumixane and isobutyl alumoxane. Among them, trialkyl aluminum is preferred and triisobutyl aluminum is particularly preferred.

The ratio of the component (a) to the component (b-1) used is that, to the unit weight (gram) of the clay or the like of the component (a), the amount of the transition metal complex of the component (b-1) is within the range of 0.01–100 mmol or, preferably, 0.1–50 mmol. The amount of the alkylating agent of the component (c) used is usually within the range of 0.1–1,000 mmol or, preferably, 10–500 mmol to the unit weight (gram) of the clay or the like of the component (a). However, even when that is used excessively, it is still possible that a suspended slurry of the clay or the like is washed with a solvent to be removed the component (c) from the system.

The ratio of the component (a) to the component (b-2) used is that, to the unit weight (gram) of the clay or the like of the component (a), the amount of the transition metal complex of the component (b-2) is within the range of 0.01–100 mmol or, preferably, 0.1–1 mmol. The amount of the alkylating agent of the component (c) used is usually within the range of 0.1–1,000 mmol or, preferably, 10–100 mmol to the unit weight (gram) of the clay or the like of the component (a). However, even when that is used excessively, it is still possible that a suspended slurry of the clay or the like is washed with a solvent to be removed the component (c) from the system.

The contacting treatment of those catalytic components may be carried out in a catalyst preparing vessel or in a reactor wherein an oligomerization reaction is conducted. Although there is no particular limitation for the conditions for that contacting treatment such as temperature, pressure, time, etc., the catalytic property which is an object of the present invention can be achieved when the treatment is carried out at the temperature of not higher than the boiling point of the solvent, at the gauge pressure of not higher than 4.0 MPa and for the time of not longer than 24 hours.

Finally, a method for the production of α-olefin according to the present invention is explained. In the method of the production of α-olefin according to the present invention, an oligomerization reaction of ethylene is carried out using a catalyst which is prepared as mentioned already and, in the presence of the above-mentioned component (c) as required. There is no particular limitation for carrying out this reaction but a solution reaction method using a solvent and any of the method where substantially no solvent is used such as a liquid-phase solvent-free reaction method and a gas-phase reaction method may be adopted and any of continuous and batch reactions may be used. When a solvent is used, examples of the solvent are hydrocarbon solvents such as pentane, hexane, heptane, cyclohexane, benzene and toluene. Each of the solvents may be used solely or two or more of them may be used by mixing thereof.

It is advantageous in terms of reaction activity that the amount of the catalyst used therefor per liter of the solvent when a solvent is used is usually within the range of 0.1–1,000 μmol or, preferably, 1–500 μmol in the case of (b-1) while, in the case of (b-2), the amount per liter of the solvent is usually within the range of 0.1–100 μmol or, preferably, 1–20 μmol.

Although there is no particular limitation for the reaction condition, the reaction temperature is usually within the range of from −78° C. to 200° C. or, preferably, from ambient temperature to 150° C. Pressure of ethylene in the reaction system is usually within the range of from an atmospheric pressure to 15 MPa or, preferably, from an atmospheric pressure to 5 MPa. Adjustment of the molecular weight during the reaction may be carried out by known means such as selection of temperature and pressure or introduction of hydrogen.

Now, the present invention will be specifically illustrated by way of the following examples although the present invention is never limited by those examples.

EXAMPLE 1

(1) Preparation of a Chemically-treated Clay Mineral A

Commercially available montmorillonite (Kunipia F; manufactured by Kunimine Kogyo) (40 g) was disintegrated for 4 hours using a disintegrating machine. The disintegrated montmorillonite (20 g) was placed in a 500-ml three-necked separable flask, dispersed into 100 ml of deionized water wherein 20 g of magnesium chloride hexahydrate was dissolved and treated at 90° C. for 0.5 hour with stirring. After the treatment, the solid component was washed with water. The treatment with magnesium chloride and washing with water were repeated once again to give a magnesium chloride-treated montmorillonite. Then this was dispersed into 160 ml of a 6% aqueous solution of hydrochloric acid and treated under refluxing for 2 hours with stirring. After the treatment, washing with water was repeated until the filtrate became neutral and the resulting clay slurry was filtered with pressure.

The filtrate was dried in vacuo at ambient temperature for 18 hours to give a chemically treated clay mineral A. Water content of the chemically treated clay mineral A was 15% by weight. Incidentally, measurement of the water content was carried out in such a manner that the dried chemically treated clay mineral was placed in a muffle furnace, the temperature was raised to 150° C. within 30 minutes and the water content was calculated from a decrease in the weight of the clay mineral obtained by keeping at the above-mentioned temperature for 1 hour.

(2) Preparation of a Clay Mineral Slurry B Treated with a Silane Compound

To a 300-ml Schlenk's tube were added 1.0 g of a chemically treated clay mineral A (water content: 15% by weight) and 50 ml of toluene to give a slurry of clay mineral. Di-n-hexylsilyl dichloride (0.96 g; 3.6 mmol) was gradually dropped, during 15 minutes, into the slurry of clay mineral with stirring. After dropping, the mixture was stirred at ambient temperature in a nitrogen stream for three days. After that, the mixture was heated at 100° C. for 1 hour and washed with 200 ml of toluene twice. The resulting slurry was added to 25 ml of a solution of tributyl aluminum in toluene (0.5 mol/liter), heated at 100° C. for 1 hour and washed with 200 ml of toluene twice and the total volume was adjusted to 50 ml with toluene to prepare a slurry B of finely dispersed clay mineral treated with a silane compound.

(3) Preparation of a Transition Metal Catalyst

Bis(cyclopentadienyl)zirconium dichloride (29 mg) was added, at ambient temperature, to 0.5 ml of a slurry B of clay mineral treated with a silane compound and stirred at room temperature for 0.5 hour whereupon 0.5 ml of a prepared catalyst solution C-1 (a catalyst containing 10 mg of clay mineral) was prepared.

(4) Oligomerization Reaction of Ethylene

To a one-liter autoclave were added 400 ml of toluene and 1.0 ml of a solution of triisobutyl aluminum in toluene (1.0 mmol/ml) and the mixture was heated to 115° C. Then 0.5 ml of the prepared catalyst solution C-1 (a catalyst containing 10 mg of clay mineral) prepared in Example 1(3) was poured thereinto and the reaction was carried out for 60 minutes together with a continuous supply of ethylene so that the pressure was able to be maintained at 3.5 MPa. After that, the reaction was stopped by adding an aqueous solution (1.0 mol/liter) of sodium hydroxide.

The total volume of the unreacted ethylene and a part of the produced 1-butene and 1-hexene was measured by a wet flowmeter and then the components were analyzed and quantitated by gas chromatography. α-Olefins in the reaction solution were quantitated by gas chromatography using n-undecane as an internal standard. Meanwhile, polymer was separated by filtration, dried at 120° C. for 12 hours and quantitated. The result was that the weight of the total products was 4.04 g. Oligomerizing activity per zirconium metal was 432 kg/g Zr/hour. The result of distribution of the resulting α-olefins is shown in Table 1.

Comparative Example 1
(1) Preparation of a Transition Metal Catalyst

Instead of addition of 29 mg of bis(cyclopentadienyl)zirconium dichloride to 0.5 ml of the slurry B of clay mineral treated with a silane compound at room temperature in Example 1(3), 60 mg of bis(cyclopentadienyl)zirconium dichloride was used as it was.

(2) Oligomerization Reaction of Ethylene

To a one-liter autoclave were added 400 ml of toluene and 1.0 ml of a solution (1.0 mmol/ml where —Al(CH$_3$)O— was calculated as one unit) of polymethylalumoxane in toluene and the mixture was heated to 115° C. Then 60 mg of bis(cyclopentadienyl)zirconium dichloride of Comparative Example 1(1) was poured thereinto and the reaction was carried out for 60 minutes together with a continuous supply of ethylene whereby the pressure was able to be maintained at 3.5 MPa. After that, the reaction was stopped by addition of an aqueous solution (1.0 mol/liter) of sodium hydroxide.

The total volume of the unreacted ethylene and a part of the produced 1-butene and 1-hexene was measured by a wet flowmeter and then the components were analyzed and quantitated by gas chromatography. α-Olefins in the reaction solution were quantitated by gas chromatography using n-undecane as an internal standard. Meanwhile, polymer was separated by filtration, dried at 120° C. for 12 hours and quantitated. The result was that the weight of the total products was 111.93 g. Oligomerizing activity per zirconium metal was 1,218 kg/g Zr/hour. The result of distribution of the resulting α-olefins is shown in Table 1.

TABLE 1

Distribution of the Products (wt %)

|  | $C_4$ | $C_6$ | $C_8$ | $C_{10}$ | $C_{12}$ | $C_{14}$ | $C_{16}$ |
|---|---|---|---|---|---|---|---|
| Example 1 | 41.4 | 33.8 | 14.7 | 2.5 | 1.1 | 0.2 | 1.7 |
| Comp. Ex. 1 | 3.9 | 5.4 | 6.8 | 6.5 | 6.7 | 6.7 | 6.7 |

|  | $C_{18}$ | $C_{20}$ | $C_{22}$ | $C_{24}$ | $C_{26}$ | $C_{28}^+$ |
|---|---|---|---|---|---|---|
| Example 1 | 1.4 | 1.1 | 0.8 | 0.8 | 0.4 | 0.0 |
| Comp. Ex. 1 | 6.6 | 6.9 | 6.2 | 6.5 | 7.3 | 23.9 |

EXAMPLE 2
(1) Preparation of a Transition Metal Catalyst

A solution (5.0 ml; 1.0 μmol/ml) of 2,6-diacetylpyridine bis(2,4-xylylimine)iron dichloride in toluene was added to 2.5 ml of the above-mentioned slurry B of clay mineral treated with a silane compound and the mixture was stirred at room temperature for 0.5 hour whereupon 7.5 ml of a prepared catalyst solution C-2 (a catalyst containing 50 mg of clay) was prepared.

(2) Oligomerization Reaction of Ethylene

To a one-liter autoclave were added 400 ml of toluene and 1.0 ml of a solution (1.0 mmol/ml) of triisobutylaluminum in toluene and the mixture was heated to 50° C. Then 7.5 ml of the prepared catalyst solution C-2 (a catalyst containing 50 mg of clay) prepared in Example 2-(1) was poured thereinto and the reaction was carried out for 30 minutes together with a continuous supply of ethylene whereby the pressure was able to be maintained at 3.5 MPa. After that, the reaction was stopped by addition of an aqueous solution (1.0 mol/liter) of sodium hydroxide.

The total volume of the unreacted ethylene and a part of the produced 1-butene and 1-hexene was measured by a wet flowmeter and then the components were analyzed and quantitated by gas chromatography. α-Olefins in the reaction solution were quantitated by gas chromatography using n-undecane as an internal standard. Meanwhile, polymer was separated by filtration, dried at 120° C. for 12 hours and quantitated. The result was that the weight of the total products was 95.06 g. Oligomerizing activity per iron metal was 681 kg/g Fe/hour. The result of distribution and purity of the resulting α-olefins is shown in Tables 2 and 3.

Comparative Example 2
(1) Preparation of a Transition Metal Catalyst

In Example 2(1), 5.0 ml of a solution (1.0 μmol/ml) of 2,6-diacetylpyridine bis(2,4-xylylimine)iron dichloride in toluene was used as it was to prepare a prepared catalyst solution D.

(2) Oligomerization Reaction of Ethylene

To a one-liter autoclave were added 400 ml of toluene and 1.0 ml of a solution (1.0 mmol/ml) of polymethylalumoxane (where —Al(CH$_3$)O— was calculated as one unit) in toluene and the mixture was heated to 50° C. Then 5.0 ml of the prepared catalyst solution D prepared in Comparative Example 2-(1) was poured thereinto and the reaction was carried out for 60 minutes together with a continuous supply of ethylene whereby the pressure was able to be maintained at 3.5 MPa. After that, the reaction was stopped by addition of an aqueous solution (1.0 mol/liter) of sodium hydroxide.

The total volume of the unreacted ethylene and a part of the produced 1-butene and 1-hexene was measured by a wet flowmeter and then the components were analyzed and quantitated by gas chromatography. α-Olefins in the reaction solution were quantitated by gas chromatography using n-undecane as an internal standard. Meanwhile, polymer was separated by filtration, dried at 120° C. for 12 hours and quantitated. The result was that the weight of the total products was 181.18 g. Oligomerizing activity per iron metal was 649 kg/g Fe/hour. The result of distribution and purity of the resulting α-olefins is shown in Tables 2 and 3.

TABLE 2

Distribution of the Products (wt %)

|  | $C_4$ | $C_6$ | $C_8$ | $C_{10}$ | $C_{12}$ | $C_{14}$ | $C_{16}$ |
|---|---|---|---|---|---|---|---|
| Example 2 | 20.2 | 17.3 | 14.4 | 9.7 | 6.8 | 5.1 | 4.0 |
| Comp. Ex. 2 | 15.0 | 15.8 | 12.4 | 8.9 | 6.6 | 5.1 | 4.1 |

|  | $C_{18}$ | $C_{20}$ | $C_{22}$ | $C_{24}$ | $C_{26}$ | $C_{28}^+$ | HWC* |
|---|---|---|---|---|---|---|---|
| Example 2 | 3.2 | 2.7 | 2.0 | 1.7 | 1.6 | 4.8 | 6.6 |
| Comp. Ex. 2 | 3.3 | 2.9 | 2.2 | 2.0 | 1.7 | 3.6 | 16.4 |

*Heavy-weight components

TABLE 3

Purity of the Products (%)

|  | $C_{10}$ | $C_{12}$ | $C_{14}$ | $C_{16}$ | $C_{18}$ |
|---|---|---|---|---|---|
| Example 2 | 98.12 | 97.49 | 97.56 | 97.30 | 96.93 |
| Comp. Ex. 2 | 96.55 | 95.93 | 95.51 | 95.29 | 94.83 |

Since the catalyst for the production of α-olefin in accordance with the present invention has a high oligomerizing activity of ethylene, production of α-olefin from ethylene can be carried out efficiently and at a low cost.

Further, in the first feature of the present invention, yields of the $C_6$, $C_8$ and $C_{10}$ components which have a big demand as industrial materials are high and, therefore, production of α-olefin can be carried out in an industrially advantageous manner.

Furthermore, in the second feature of the present invention, production of by-products such as heavy-weight components and wax components is limited and, therefore, the after-treatment after the reaction is easy. Moreover, each of the α-olefin components has a high purity and is excellent as a product.

Among the α-olefin components produced by using the catalyst of the present invention, the $C_6$ and $C_8$ components can be used as comonomer materials for the production of linear low-density polyethylene. In addition, the $C_{10}$ component is used as a material for a synthetic lubricant (poly-α-olefin)

What is claimed is:

1. A catalyst obtained by contacting (a) a clay, clay mineral or ion-exchange layer compound with (b-1) a transition metal complex of Groups 4 to 6 of the Periodic Table, wherein (a) is treated with an organosilane compound in the presence of water.

2. The catalyst according to claim 1, wherein a ligand of the transition metal complex which is the component (b-1) has a conjugated five-membered ring.

3. The catalyst according to claim 1, wherein the transition metal complex comprises zirconium.

4. The catalyst according to claim 1, wherein component (a) contains an inorganic substance containing phyllosilicate.

5. The catalyst according to claim 1, wherein component (a) comprises montmorillonite.

6. The catalyst according to claim 1, wherein the catalyst comprises clay.

7. The catalyst according to claim 1, wherein the catalyst comprises a clay mineral.

8. The catalyst according to claim 1, wherein the catalyst comprises an ion-exchange layer compound.

9. The catalyst according to claim 1, wherein the clay, clay mineral or ion-exchange layer compound comprises water before treatment with an organosilane.

10. The catalyst according to claim 1, wherein the catalyst comprises a mica, smectite or vermiculite.

11. The catalyst according to claim 1, wherein the organosilane comprises a compound having at least one alkyl group bonded to the silicon atom.

12. The catalyst according to claim 1, comprising a transition metal complex of Group 4 of the Periodic Table.

13. The catalyst according to claim 1, wherein comprising a transition metal complex of Group 5 of the Periodic Table.

14. The catalyst according to claim 1, wherein comprising a transition metal complex of Group 6 of the Periodic Table.

15. A method comprising
oligomerizing ethylene in the presence of the catalyst of claim 1.

* * * * *